United States Patent [19]

Saito et al.

[11] Patent Number: 5,041,604

[45] Date of Patent: Aug. 20, 1991

[54] PROCESS FOR PRODUCING DI(ARYLOXY) ALKANE

[75] Inventors: Toranosuke Saito, Osaka; Masakatu Kitani, Hyogo; Takashi Ishibashi, Osaka, all of Japan

[73] Assignee: Sanko Kaihatsu Kagaku Kenkyusho, Osaka, Japan

[21] Appl. No.: 540,872

[22] Filed: Jun. 20, 1990

Related U.S. Application Data

[63] Continuation of Ser. No. 134,836, Dec. 18, 1987, abandoned.

[30] Foreign Application Priority Data

Dec. 22, 1986 [JP] Japan .................................. 61-303933

[51] Int. Cl.$^5$ ............................................. C07C 255/00
[52] U.S. Cl. ......................... 558/415; 558/416; 558/420; 558/423; 558/424; 562/435; 562/463; 562/469; 562/473; 562/474; 568/306; 568/313; 568/314; 568/424; 568/433; 568/585; 568/592; 568/643; 568/644; 568/645
[58] Field of Search ............... 568/645, 644, 306, 313, 568/314, 315, 424, 433, 585, 592, 643; 562/435, 463, 469, 473, 474; 558/415, 416, 420, 423, 424

[56] References Cited

U.S. PATENT DOCUMENTS 2,130,990 9/1938 Coleman et al. .................... 568/645
3,787,506 1/1974 Ungefug et al. .................... 568/645

Primary Examiner—Bruce Gray
Attorney, Agent, or Firm—Kane, Dalsimer, Sullivan, Kurucz, Levy, Eisele and Richard

[57] ABSTRACT

A process for producing a high quality di(aryloxy)alkane with a high yield by the use of readily commercially available materials, without using any particular solvent or agent and by means of a simple operation and a general apparatus is provided, which process comprises subjecting a halogenated alkane of the formula (II)

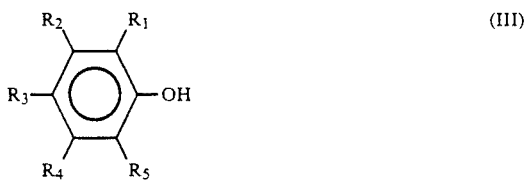

wherein X and Y each represent a halogen atom and A represents a lower alkylene group, and a phenol of the formula (III)

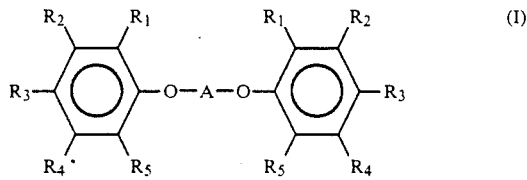

wherein
$R_1$ to $R_5$ each are same or different, represent hydrogen, halogen, lower alkyl, lower alkoxy, carboxylic acid salt, acyl or nitro group, and may form a ring in conjunction of two adjacent groups,
to condensation reaction in the presence of an alkali in an aqueous medium to form a di(aryloxy)alkane of the formula (I)

and is characterized (i) by carrying out the condensation reaction in a molar ratio of the compound of the formula (II): the phenol of the formula (III): the alkali in terms of monovalent base of 1:1.5 to 3.0:1.5 to 3.0; or
(ii) by carrying out the condensation reaction of the above (i) and adjusting the quantity of the aqueous medium phase after completion of the reaction can be 35% or less based on the oily phase; or
(iii) by carrying out the condensation reaction of the above (i), feeding at least the alkali among the reaction components with progress of the reaction and adjusting the quantity of the aqueous medium phase as described in the above (ii).

3 Claims, No Drawings

PROCESS FOR PRODUCING DI(ARYLOXY) ALKANE

This is a continuation of co-pending application Ser. No. 134,836 filed on Dec. 18, 1987 now abandoned.

BACKGROUND OF THE INVENTION

1. Field of the Invention

This invention relates to a process for producing a di(aryloxy)alkane commercially and advantageously.

2. Description of the Related Art

Di(aryloxy)alkanes have various application fields such as sensitizers for heat-sensitive recording materials, heat-fusibilizing agents, monomer raw materials for synthetic high-molecular weight compounds, particularly polyester resins, additives such fire retardants, etc., and various production processes have been proposed, but no fully satisfactory processes have yet been found.

For example, according to a process (Bulletin of Industrial Chemistry, vol. 66, pp 979-981), ethylene dichloride and phenol and NaOH both of 10 mols per mol of the chloride are reacted in an aqueous medium under reflux to obtain diphenoxyethane with a yield of 72% based on ethylene chloride, but in order to recover a large excess of phenol, considerable agents, equipments, energy, labor, etc. are required.

Further, according to a process of reacting a sulfonic acid ester of an aryloxyalkanol with an aromatic alcohol (Japanese Patent Application Laid-open No. Sho 61-122238/1986), steps of converting a phenol into an aryloxyalkanol, followed by converting it into a sulfonic acid ester are required; hence this process cannot be regarded as a good countermeasure in the production of a di(aryloxy)alkane of symmetric type.

The present inventors have further made extensive research on use of various solvents or mixtures of solvents with water as a reaction medium or various acid-seizing agents, additives, etc., but any of these substances have yielded no commercially satisfactory results.

SUMMARY OF THE INVENTION

The object of the present invention is to provide a process for producing a high quality di(aryloxy)alkane with a high yield by the use of readily commercially available materials, without using any particular solvent or agent, and by means of a simple operation and a general apparatus.

The present invention resides in the following process.

in the production of a di(aryloxy)alkane by subjecting a dihalogenated alkane expressed by the formula (II)

$$X-A-Y \quad (II)$$

wherein X and Y each represent a halogen atom and A represents a lower alkylene group, and a phenol expressed by the formula (III)

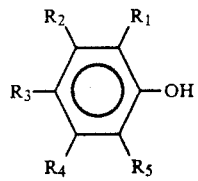

(III)

wherein $R_1$ to $R_5$ each are the same or different from one another; each represent hydrogen atom, a halogen atom, a lower alkyl group, a lower alkoxy group, a carboxylic acid salt group, an acyl group, cyano group, a cycloalkyl group, an aryl group or nitro group; and may form a ring in conjunction of two adjacent groups, to condensation reaction on heating in the presence of an alkali in an aqueous medium to form a di(aryloxy)alkane expressed by the formula (I)

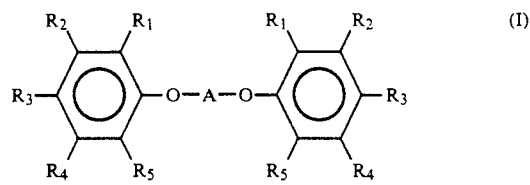

wherein A and $R_1$ to $R_5$ are as defined in the above formulas (II) and (III), a process characterized by carrying out said condensation reaction in a molar ratio of said dihalogenated alkane of the formula (II): said phenol of the formula (III): said alkali (in terms of a monovalent base) of 1:1.5 to 3.0:1.5 to 3.0 and by adjusting the quantity of the phase of said aqueous medium after completion of said condensation reaction so as to give 35% by weight or less based on the quantity of the oily phase present in the reaction mixture.

Further, the present invention is characterized in that at least said alkali among the reaction components in said ratio is fed with progress of said condensation reaction.

DETAILED DESCRIPTION OF PREFERRED EMBODIMENTS

In the present invention, as the molar ratio of a dihalogenated alkane: a phenol: an alkali (in terms of a monovalent base), 1:1.5 to 3.0:1.5 to 3.0 i.e. the respective theoretical quantities of these three components or quantities close thereto are employed, the components are reacted using substantially water as a medium for the reaction, and further, the reaction is carried out by additionally adding at least an alkali among the raw materials with progress of the condensation reaction, whereby it is possible to prevent decomposition of the dihalogenated alkane (and a monohalogenated monoaryloxyalkane as a reaction intermediate) to thereby improve the yield. Still further, the quantity of the aqueous phase is controlled to 35% or less based on the quantity of the oily phase, whereby it is possible to notably promote the reaction rate, particularly the reaction rate since a period close to the final period of the reaction. When the above-mentioned specific means are together employed, it is possible to obtain the objective di(aryloxy)alkane with a high quality and a high yield and in a shortened time.

The reason for the foregoing is presumed as follows:

The dihalogenated alkane is reacted with the phenol in the presence of an alkali in an aqueous phase.

As to the regulation of the quantity of an alkali added, when the dihalogenated alkane, particularly a dihalogenated alkane having halogen atoms bonded to adjacent carbon atoms, is used as a raw material, the above regulation has an effectiveness that byproduction of unsaturated compounds due to intramolecular dehydrochlorination reaction is inhibited to notably improve the yield of the objective compound. (For example, in the case of 1,2-ethylene dichloride, byproduction of vinyl chloride is notably inhibited.)

Further, the regulation of the quantity of the aqueous phase regulates the concentration of alkali metal salts of the phenol (hereinafter referred to as "phenolates") dissolved in the aqueous phase in combination with the above regulation of the quantity of an alkali added, but the phenolates solubilize the dihalogenated alkane (and monohalogenated monoaryloxyalkane) into the aqueous phase in an aqueous solution state to advance condensation reaction. Although the solubilizability thereof varies depending on the kind of the phenolates, it becomes sufficient when the concentration thereof in the aqueous phase has increased up to a certain value or higher, but if the concentration is lower than the value, the solubilizability is low so that the effectiveness of promoting the reaction rate is small. However, it is considered that if the concentration exceeds a certain limit, the phenolates are deposited to contrarily inhibit the reaction rate and also promote decomposition of the dihalogenated alkane.

Thus it is considered that at the stage where unreacted phenol is present in a considerably large quantity, somewhat large quantities of the alkali and the aqueous phase are advantageous for promoting the reaction, whereas at the stage where the reaction has advanced and the quantity of the phenol has been reduced, it is necessary for promoting the reaction to regulate the quantities of the alkali and the aqueous phase.

Namely, at the initial period of the reaction, it is advantageous that the quantity of the aqueous phase is large to such an extent that the concentration of the alkali (i.e. the concentration of the phenolates) is not so small as to reduce the reaction rate, whereas as the reaction advances and the remaining quantity of the phenol is reduced, the quantity of the aqueous phase is reduced and water is removed to the outside of the reaction system so that the concentration of the phenolates dissolved in the aqueous phase may not be reduced as much as possible, whereby the reaction rate particularly at the period close to the final period of the reaction is promoted. In the case where the phenolates have a low solubilizability, addition of a surfactant, particularly an anionic surfactant, is effective for preventing reduction in the reaction rate at the period close to the final period of the reaction.

However, since the dihalogenated alkane is solubilized by the phenolates to react in the aqueous phase, the total quantity of reacted materials corresponds to the product of the reaction rate by the aqueous phase in which the reaction is carried out; hence it is contrarily disadvantageous to extremely reduce the quantity of the aqueous phase.

In view of the foregoing, it is preferred to adjust the quantity of the aqueous phase in the reaction mixture system to 30 to 70%, preferably 35 to 60% at the initial period to the intermediate period of the reaction.

Further, in the case where the alkali is an alkali metal hydroxide, it is presumed to be present as an alkali metal salt of the phenol in the reaction mixture, and its concentration in the aqueous phase in the reaction system is preferred to be always kept at 20 molar concentration or lower, preferably 12 molar concentration or lower.

Next, the present invention will be described referring to a general embodiment.

Into a reactor are introduced a water dihalogenated alkane and a phenol, followed by adding an alkali in a portion of the total quantity required (e.g. 30 to 70%) with stirring and then heating the mixture under mild reflux.

As to the total quantities of the respective raw materials used, the quantity of the phenol is 1.5 to 3.0 mols, preferably 1.8 to 2.3 mols based on one mol of the dihalogenated alkane and the total quantity of the alkali is 1.5 to 3.0 mols, preferably 2.0 to 2.5 mols based thereon. As to the alkali, it is preferred to use an alkali metal hydroxide in the form of its aqueous solution.

As to the molar ratio of the phenol to the alkali, there is no particular necessity that it is made 1:1 or close thereto. If the molar ratio of the phenol is lower than the above range, the yield lowers, while even if it exceeds the range, there is no particular merit.

Further, if the molar ratio of the alkali is lower than the above range, the reaction rate at the latter period of the reaction lowers, the conversion is low and the yield lowers, while if it exceeds the range, the conversion increases, but decomposition of the dihalogenated alkane (and the monohalomonoaryloxyalkane) increases and the yield and quality lower.

Next, after the residual quantity of the alkali has been gradually added or while it is gradually added, the reflux condenser is changed over to an effluent cooler equipped with an oil-water separator, whereby the aqueous layer in the resulting condensate is removed to the outside of the system, while the oily layer (the dihalogenated alkane and monohaloaryloxyalkane) is returned to the inside of the reactor, and water is flown out so that the quantity of the aqueous layer in the reactor can be 35% or less, preferably 10 to 25%, based on the quantity of the oily layer. (This quantity can be calculated from the quantities of the raw materials fed, the quantity of water and the quantity of water flown out.) If the quantity of the aqueous phase is less than the above range, the crystal concentration of the salt formed increases, obstacles to agitation and heat transfer are liable to occur, while the quantity exceeds the range, the reaction rate lowers to retard the reaction time or the yield lowers. The total reaction time is in the range of 10 to 40 hours, usually 13 to 20 hours.

A process of additionally adding the dihalogenated alkane along with the alkali is also preferred.

Further, if the reaction is carried out while the deposited salt is successively removed to the outside of the reaction system, it is possible to further reduce the quantity of the aqueous phase, but in this case it is necessary to pay attention particularly to the loss of the phenolates.

The salt formed after completion of the reaction is filtered off, or if necessary, water is added to the reaction mixture to reduce the salt concentration, followed by separating the aqueous layer, washing the oily layer with water and drying it. Since the oily layer is the objective product and generally has a melting point higher than room temperature, it is treated while its temperature is kept.

If purification is required for the oily layer, the layer is subjected to vacuum distillation, or subjected to such purification treatments that it is dissolved in a suitable solvent on heating and if desired, decolorizing carbon is added, followed by filtering off it while hot, and further subjecting it to cooling, crystallization, separation, etc.

At the time of the condensation reaction, it is also possible to simultaneously use a surfactant or use a suitable additive for depressing the melting point of the condensation product.

Examples of the dihalogenated alkane expressed by the formula (II) in the present invention are methylene dichloride, 1,2-ethylene dichloride, 1,2- or 1,3-propylene dichloride, 1,2-, 1,3- or 1,4-butylene dichloride or monochloromonobromo-compounds or dibromo-compounds of the foregoing, etc. Further, examples of the phenol expressed by the formula (III) are phenol, 2-, 3- or 4-cresol, 2,3-, 2,4-, 2,5-, 2,6-, 3,4-, 3,5- or 3,6-xylenol, 2,3,5-, 2,3,6- or 2,4,6-trimethylphenol, 2- or 4-ethylphenol, 2-, 3- or 4-t-butylphenol, 2-, 3- or 4-methoxyphenol, 2- or 4-chlorophenol, 2,4- or 2,6-dichlorophenol, 2-chloro-4-methylphenol, 2-methyl-4-chlorophenol, 2-, 3- or 4-nitrophenol, 2- or 4-acetylphenol, 2- or 4-benzoylphenol, 2- or 4-cyanophenol, sodium 3- or 4-hydroxybenzoate, 2- or 4-cyclohexylphenol, o- or p-phenylphenol, 1- or 2-naphthol, 2-isopropyl-2-naphthol, sodium 2-hydroxy-6-naphthoate, etc.

The present invention will be described in more detail by way of Examples.

EXAMPLE 1

Ethylene dichloride (95 g), m-cresol (200 g) and water (35 ml) were introduced into a reactor, followed by dropwise adding a 49% aqueous solution of NaOH (106 g) in nitrogen gas atmosphere with stirring over about 20 minutes, heating the mixture under mild reflux for 3 hours, dropwise adding a 49% aqueous solution of NaOH (77 g) over 8 hours, and further continuing reaction for 8 hours. The temperature inside the reactor was about 110° C. Thereafter water (185 ml) was added, followed by agitating the mixture at 100° C., allowing it to stand still, thereafter separating the aqueous layer, again adding water (35 ml), agitating the mixture, allowing it to stand still, separating the resulting oily layer, adding isopropanol (580 ml) to the layer, dissolving the layer therein at 85° to 90° C., filtering it while hot, cooling, crystallizing, filtering, washing with isopropanol and drying to obtain 1,2-di(3-methylphenoxy)ethane (153 g) in the form of colorless plate crystals. Yield: 68.3% based on m-cresol. M.P.: 98.0° C. Purity: 99.4%.

COMPARATIVE EXAMPLE 1

Ethylene dichloride (95 g, 0.96 mol), m-cresol (200 g, 1.85 mol) and water (35 ml) were introduced into a reactor, followed by dropwise adding a 49% (by weight; this applies to the subsequent %) aqueous solution of NaOH (183 g, 2.24 mol) over about 20 minutes while the mixture was agitated in nitrogen gas atmosphere, and subjecting the mixture to condensation reaction under mild reflux for 20 hours (the quantity of the aqueous phase in the reactor being calculated to be about 46% based on the quantity of the oily phase). The temperature inside the reactor was about 110° C. Thereafter post-treatment was carried out in the same manner as in Example 1 to obtain 1,2-di(3-methylphenoxy)ethane in the form of colorless plate crystals (115 g). Yield: 51.3 g. M.P.: 97.7° C. Purity: 99.1%.

EXAMPLE 2

Ethylene dichloride (95 g), m-cresol (200 g) and water (35 ml) were introduced into a reactor, followed by dropwise adding a 49% aqueous solution of NaOH (106 g) over 20 minutes with stirring in nitrogen gas atmosphere, thereafter heating the mixture under mild reflux for 3 hours, dropwise adding a 49% aqueous solution of NaOH (77 g) over 8 hours, thereafter changing over the reflux condenser to an effluent condenser equipped with an oil-water separator, removing the aqueous phase in the condensate to the outside of the system, returning the oily layer to the reactor and continuing the condensation reaction. After 4 hours, the quantity of effluent water was 95 ml and the reaction temperature inside the reactor reached 120° C. The quantity of the aqueous phase in the reactor was calculated to be about 30% based on the quantity of the oily phase. Thereafter, post-treatment was carried out in the same manner as in Example 1, to obtain 1,2-di(3-methylphenoxy)ethane in the form of colorless plate crystals (163 g). Yield: 72.8% based on m-cresol. M.P.: 98.2° C. Purity: 99.6%.

Using phenols indicated in Table 1 in place of m-cresol (200 g, 1.85 mol), operation was carried out in the same manner as in Example 2, to obtain the corresponding 1,2-di(aryloxy)ethanes.

TABLE 1

| Phenols | Compounds obtained | M.P. (°C.) |
|---|---|---|
| Phenol | 1,2-Di(phenoxy)ethane | 96 |
| o-Cresol | 1,2-Di(2-methylphenoxy)ethane | 84 |
| p-Cresol | 1,2-Di(4-methylphenoxy)ethane | 135 |
| 2,3-Xylenol | 1,2-Di(2,3-dimethylphenoxy)ethane | 120 |
| 3,4-Xylenol | 1,2-Di(2,4-dimethylphenoxy)ethane | 111.5 |
| 2,5-Xylenol | 1,2-Di(2,5-dimethylphenoxy)ethane | 80 |
| 3,4-Xylenol | 1,2-Di(3,4-dimethylphenoxy)ethane | 105 |
| 4-Ethylphenol | 1,2-Di(4-ethylphenoxy)ethane | 151.5 |
| 4-Methoxyphenol | 1,2-Di(4-methoxyphenoxy)ethane | 128 |
| 4-Chlorophenol | 1,2-Di(4-chlorophenoxy)ethane | |
| 1-Naphthol | 1,2-Di(1-naphthoxy)ethane | 129 |

EXAMPLE 3

Operation was carried out in the same manner as in Example 2, using 1,3-propylene dichloride (108 g, 0.96 mol), p-cresol (205 g, 1.90 mol), water (35 ml) and a 49% aqueous solution of NaOH (106 g, 1.30 mol; a first dropwise addition) and further 79 g, 0.97 mol (a second dropwise addition), to obtain 1,3-di(4-methylphenoxy)-propane in the form of white plate crystals (178 g). Yield: 73.2% based on p-cresol. M.P.: 93.5° C. Purity: 99.6%.

EXAMPLE 4

Operation was carried out in the same manner as in Example 2, using 1,4-butylene dichloride (122 g, 0.96 mol), phenol (174 g, 1.85 mol), water (40 ml) and a 49% aqueous solution of NaOH (106 g) (a first dropwise addition) and (77 g) (a second dropwise addition), to obtain 1,4-di(phenoxy)butane in the form of white plate crystals (188 g). Yield: 83.9% based phenol. M.P.: 99° C. Purity: 99.0%.

Further, operation was similarly carried out using p-cresol (200 g) in place of phenol (174 g) to obtain 1,4-di(4-methylphenoxy)butane (208 g) in the form of white plate crystals. Yield: 83.2% based on p-cresol. M.P.: 104° C. Purity: 99.1%.

What is claimed is:
1. In a process for the preparation of di(aryloxy) compounds of the formula:

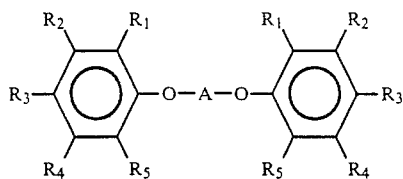 (I)

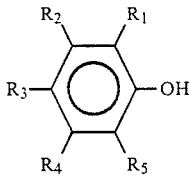 (III)

wherein A is a lower alkylene group and each $R_1$ to $R_5$ may be the same or different and independently are selected from the group consisting of a hydrogen atom, a halogen atom, a lower alkyl group, a lower alkoxy group, a carboxylic acid salt group, an acyl group, a cyano group, a cycloalkyl group, an aryl group and a nitro group and two adjacent groups of $R_1$ to $R_5$ when together from a divalent cyclic moiety, by a condensation reaction between a dihalogenated compound represented by the Formula $$X-A-Y \qquad (II)$$

wherein X and Y each represent a halogen atom and A is as defined above; and a phenol represented by the Formula wherein $R_1$ to $R_5$ are as defined above; in the presence of a base in an aqueous, the improvement which comprises; carrying out said condensation reaction in a molar ratio of said dihalogenated compound: phenol: base of 1:1.5 to 3.0:1.5 to 3.0, and adding, the base gradually during the condensation the reaction; and maintaining the proportion of aqueous medium phase in the reaction mixture at 35% by weight or less based on the quantity of the oily phase present in the reaction mixture.

2. A process of claim 1 wherein an alkali metal hydroxide or an aqueous solution thereof is used as said base.

3. A process of claim 1 wherein said condensation reaction is carried out in the presence of an anionic surfactant.

* * * * *